(12) United States Patent
Yoshizaki et al.

(10) Patent No.: US 10,299,665 B2
(45) Date of Patent: May 28, 2019

(54) IMAGING DEVICE AND CAPSULE ENDOSCOPE SYSTEM

(71) Applicant: OLYMPUS CORPORATION, Hachioji-shi, Tokyo (JP)

(72) Inventors: Kazunori Yoshizaki, Hachioji (JP); Ken Ioka, Hachioji (JP); Sunao Kikuchi, Akiruno (JP); Yasuhiro Komiya, Sagamihara (JP); Yasuhiro Fukunaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 77 days.

(21) Appl. No.: 15/616,340

(22) Filed: Jun. 7, 2017

(65) Prior Publication Data
US 2017/0265731 A1 Sep. 21, 2017

Related U.S. Application Data

(63) Continuation of application No. PCT/JP2014/083180, filed on Dec. 15, 2014.

(51) Int. Cl.
*A61B 1/04* (2006.01)
*A61B 1/06* (2006.01)
(Continued)

(52) U.S. Cl.
CPC ............... *A61B 1/041* (2013.01); *A61B 1/00* (2013.01); *A61B 1/00009* (2013.01);
(Continued)

(58) Field of Classification Search
CPC ..... A61B 1/041; A61B 1/0638; A61B 1/0646; A61B 1/00016; A61B 1/00009;
(Continued)

(56) References Cited

U.S. PATENT DOCUMENTS

2011/0273548 A1* 11/2011 Uchiyama .......... A61B 1/00009
348/68
2012/0157774 A1 6/2012 Kaku
(Continued)

FOREIGN PATENT DOCUMENTS

| JP | 2011041758 A | 3/2011 |
| JP | 2012125395 A | 7/2012 |

(Continued)

OTHER PUBLICATIONS

International Search Report (ISR) and Written Opinion dated Mar. 24, 2015 issued in International Application No. PCT/JP2014/083180.

*Primary Examiner* — Jared Walker
(74) *Attorney, Agent, or Firm* — Holtz, Holtz & Volek PC

(57) ABSTRACT

An imaging device includes: an imaging sensor; a color filter including first band filters and a second band filter configured to transmit narrowband light having a maximum value of a transmission spectrum outside a range of the wavelength band of the light that passes through each first band filter; a first light source unit; a second light source unit configured to radiate light having an upward projecting distribution of a wavelength spectrum in relation to intensity and having a narrowband light spectrum narrower than the broadband; and a control unit configured to cause the first light source unit and the second light source unit to radiate the beams of light simultaneously, wherein a peak wavelength of the light radiated by the second light source unit is an infrared region or a near-infrared region.

6 Claims, 13 Drawing Sheets

(51) Int. Cl.
  *H04N 9/47* (2006.01)
  *A61B 1/00* (2006.01)
  *H04N 5/225* (2006.01)
  *H04N 5/33* (2006.01)
  *H04N 9/04* (2006.01)

(52) U.S. Cl.
  CPC ........ *A61B 1/00016* (2013.01); *A61B 1/0638* (2013.01); *A61B 1/0646* (2013.01); *H04N 5/2252* (2013.01); *H04N 5/2256* (2013.01); *H04N 5/33* (2013.01); *H04N 5/332* (2013.01); *H04N 9/045* (2013.01); *H04N 2005/2255* (2013.01); *H04N 2209/047* (2013.01)

(58) Field of Classification Search
  CPC ............ A61B 1/00; H04N 5/332; H04N 5/33; H04N 5/2256; H04N 9/045; H04N 5/2252; H04N 2209/047; H04N 2005/2255
  USPC .......................................................... 348/68
  See application file for complete search history.

(56) References Cited

U.S. PATENT DOCUMENTS

| | | | |
|---|---|---|---|
| 2013/0265401 A1* | 10/2013 | Igarashi | A61B 1/0661 348/68 |
| 2014/0031628 A1 | 1/2014 | Kaku | |
| 2014/0316195 A1 | 10/2014 | Kaku et al. | |
| 2016/0077008 A1 | 3/2016 | Takasu et al. | |

FOREIGN PATENT DOCUMENTS

| | | |
|---|---|---|
| JP | 2013039224 A | 2/2013 |
| JP | 2013128686 A | 7/2013 |
| JP | 2013150712 A | 8/2013 |
| JP | 2014023591 A | 2/2014 |
| JP | 2014033777 A | 2/2014 |
| JP | 2014212801 A | 11/2014 |
| WO | 2010143692 A1 | 12/2010 |

* cited by examiner

IMAGING DEVICE AND CAPSULE ENDOSCOPE SYSTEM

CROSS REFERENCES TO RELATED APPLICATIONS

This application is a continuation of PCT international application Ser. No. PCT/JP2014/083180 filed on Dec. 15, 2014, which designates the United States, incorporated herein by reference.

BACKGROUND

The present disclosure relates to an imaging device and a capsule endoscope system.

In recent years, a technique of displaying capillaries in a superficial portion of a mucous membrane and a fine pattern of the mucous membrane has been known in the field of endoscopes (refer to JP 2012-125395 A). Specifically, light in a narrowband (hereinafter referred to as "narrowband light") that is narrower than a white wavelength band and included in each of blue and green wavelength bands is radiated to an observed region of a subject, and an image is produced from reflected light reflected at the observed region. In this technique, blue narrowband light, green band light, and red band light are sequentially radiated, whereby a colored normal image and a special image are simultaneously acquired, and the capillaries in the superficial portion of the mucous membrane and the fine pattern of the mucous membrane may be observed in the special image.

SUMMARY

An imaging device according to one aspect of the present disclosure includes: an imaging sensor configured to perform a photoelectric conversion on light received by each of a plurality of pixels arranged in a two-dimensional pattern to generate an electric signal; a color filter in which a filter unit including a plurality of first band filters and a second band filter is arranged in association with the plurality of pixels, each of the first band filters being configured to transmit light in a wavelength band of a primary color or a complementary color, the second band filter being configured to transmit narrowband light having a maximum value of a transmission spectrum outside a range of the wavelength band of the light that passes through each of the plurality of first band filters; a first light source unit configured to radiate broadband light including a range of a transmission spectrum of each of the plurality of first band filters; a second light source unit configured to radiate light having an upward projecting distribution of a wavelength spectrum in relation to intensity and having a narrowband light spectrum narrower than the broadband, the light being radiated such that an upper limit value and a lower limit value of a wavelength that are half a maximum value in the light spectrum are between an upper limit value and a lower limit value of a wavelength that are half the maximum value in the transmission spectrum of the second band filter; and a control unit configured to cause the first light source unit and the second light source unit to radiate the beams of light simultaneously, wherein a peak wavelength of the light radiated by the second light source unit is an infrared region or a near-infrared region.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the present disclosure will be described in detail with reference to the drawings. The present disclosure is not limited by the following embodiments. In each drawing that is referred to in the following description, a shape, a size, and a positional relation are only schematically illustrated to such an extent that contents of the present disclosure may be understood. Therefore, the present disclosure is not limited only to the shape, the size, and the positional relation represented in each drawing. The following description is based on an example of a capsule endoscope system including a capsule endoscope that is introduced into a subject to capture an in-vivo image of the subject and a processing device that receives a wireless signal from the capsule endoscope to display the in-vivo image of the subject. However, the present disclosure is not limited by this embodiment. Identical components are denoted by the same reference signs for illustration.

First Embodiment

Schematic Configuration of Capsule Endoscope System

Figure 1:
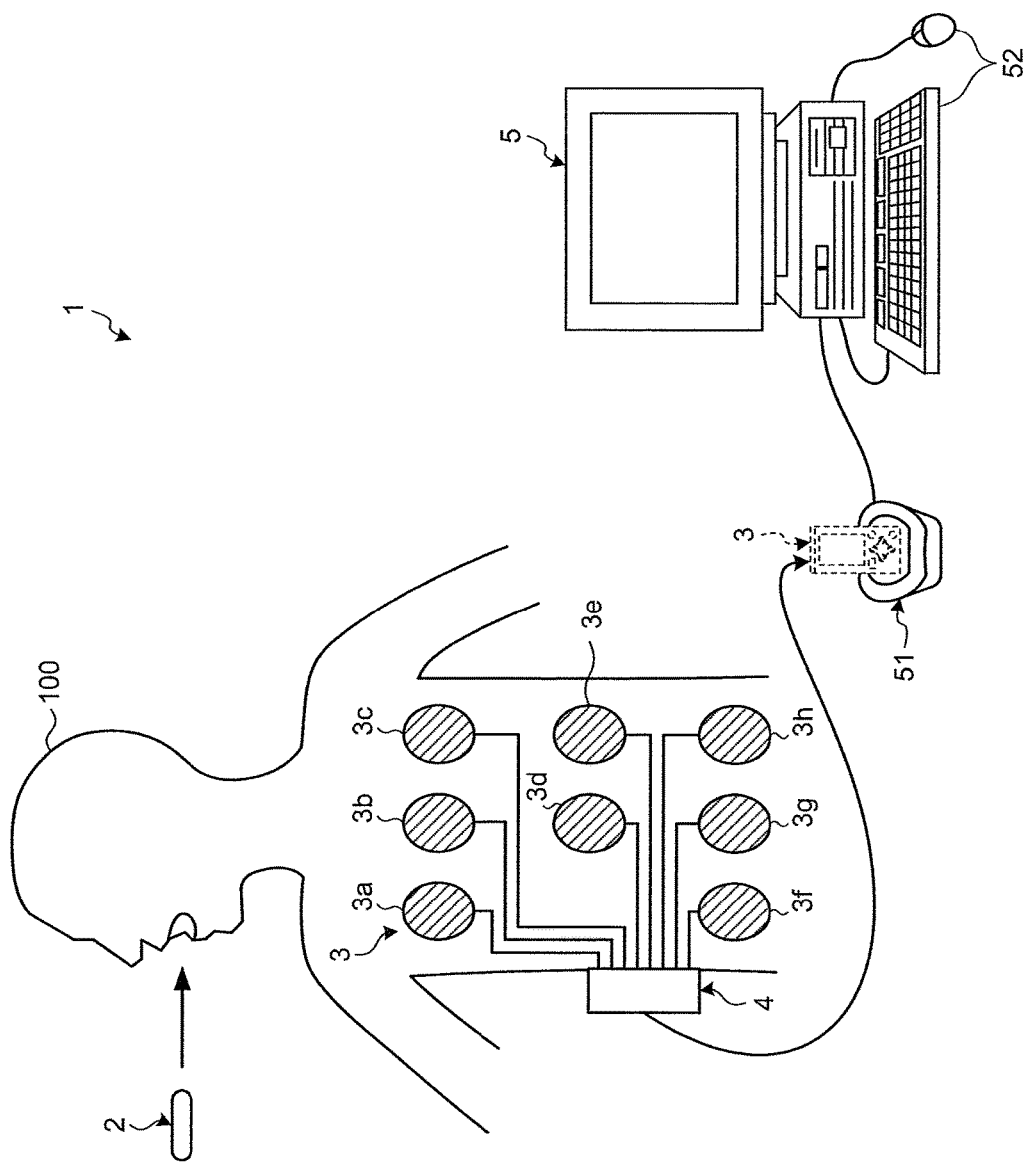
FIG. 1 is a schematic diagram illustrating an overview configuration of a capsule endoscope system according to a first embodiment of the present disclosure.

FIG. 1 is a schematic diagram illustrating an overview configuration of a capsule endoscope system according to a first embodiment of the present disclosure.

A capsule endoscope system 1 illustrated in FIG. 1 includes a capsule endoscope 2, a receiving antenna unit 3, a receiving device 4, and an image processing device 5. The capsule endoscope 2 captures an in-vivo image of a subject 100. The receiving antenna unit 3 receives a wireless signal sent from the capsule endoscope 2 introduced into the subject 100. The receiving antenna unit 3 is detachably connected to the receiving device 4. The receiving device 4 performs a predetermined process on the wireless signal received by the receiving antenna unit 3 for recording and display. The image processing device 5 processes and/or displays an image corresponding to image data of the inside of the subject 100 captured by the capsule endoscope 2.

The capsule endoscope 2 has an imaging function of capturing the inside of the subject 100 and a wireless communication function of sending, to the receiving antenna unit 3, in-vivo information including the image data obtained by capturing the inside of the subject 100. The capsule endoscope 2 is swallowed into the subject 100 to pass through an esophagus in the subject 100 and move through a body cavity of the subject 100 with the aid of a peristaltic movement of a digestive lumen. The capsule endoscope 2 sequentially captures the inside of the body cavity of the subject 100 at very small time intervals, for example, at intervals of 0.5 seconds (2 fps), while moving through the body cavity of the subject 100. The capsule endoscope 2 then generates pieces of image data of the inside of the subject 100 captured, and sequentially sends the pieces of image data to the receiving antenna unit 3. A detailed configuration of the capsule endoscope 2 will be described later.

The receiving antenna unit 3 includes receiving antennas 3a to 3h. Each of the receiving antennas 3a to 3h receives the wireless signal from the capsule endoscope 2 and sends the wireless signal to the receiving device 4. Each of the receiving antennas 3a to 3h is configured with the use of a loop antenna and arranged at a predetermined position on an outer surface of the subject 100, for example, at a position corresponding to each organ in the subject 100 through which the capsule endoscope 2 passes.

The receiving device 4 records the image data of the inside of the subject 100 included in the wireless signal sent from the capsule endoscope 2 through the receiving antennas 3a to 3h, or displays the image corresponding to the image data of the inside of the subject 100. The receiving device 4 records, for example, positional information of the capsule endoscope 2 and time information indicating time in association with the image data received through the receiving antennas 3a to 3h. The receiving device 4 is contained in a receiving device holder (not illustrated) and carried by the subject 100 while an examination is performed using the capsule endoscope 2, for example, while the capsule endoscope 2 is introduced through a mouth of the subject 100, passes through a digestive tract, and is discharged from the subject 100. The receiving device 4 is removed from the subject 100 after the end of the examination with the capsule endoscope 2, and connected to the image processing device 5 for transferring the image data or the like received from the capsule endoscope 2.

The image processing device 5 displays the image corresponding to the image data of the inside of the subject 100 acquired through the receiving device 4. The image processing device 5 includes a cradle 51 that reads the image data or the like from the receiving device 4 and an operation input device 52 such as a keyboard and a mouse. When the receiving device 4 is attached, the cradle 51 acquires, from the receiving device 4, the image data and related information associated with the image data such as the positional information, the time information, and identification information of the capsule endoscope 2. The cradle 51 then transfers the acquired items of information to the image processing device 5. The operation input device 52 accepts input from a user. The user makes a diagnosis for the subject 100 by observing a body part inside the subject 100, e.g., an esophagus, a stomach, a small intestine, and a large intestine, while operating the operation input device 52 and watching the images of the inside of the subject 100 sequentially displayed by the image processing device 5.

Configuration of Capsule Endoscope

Figure 2:
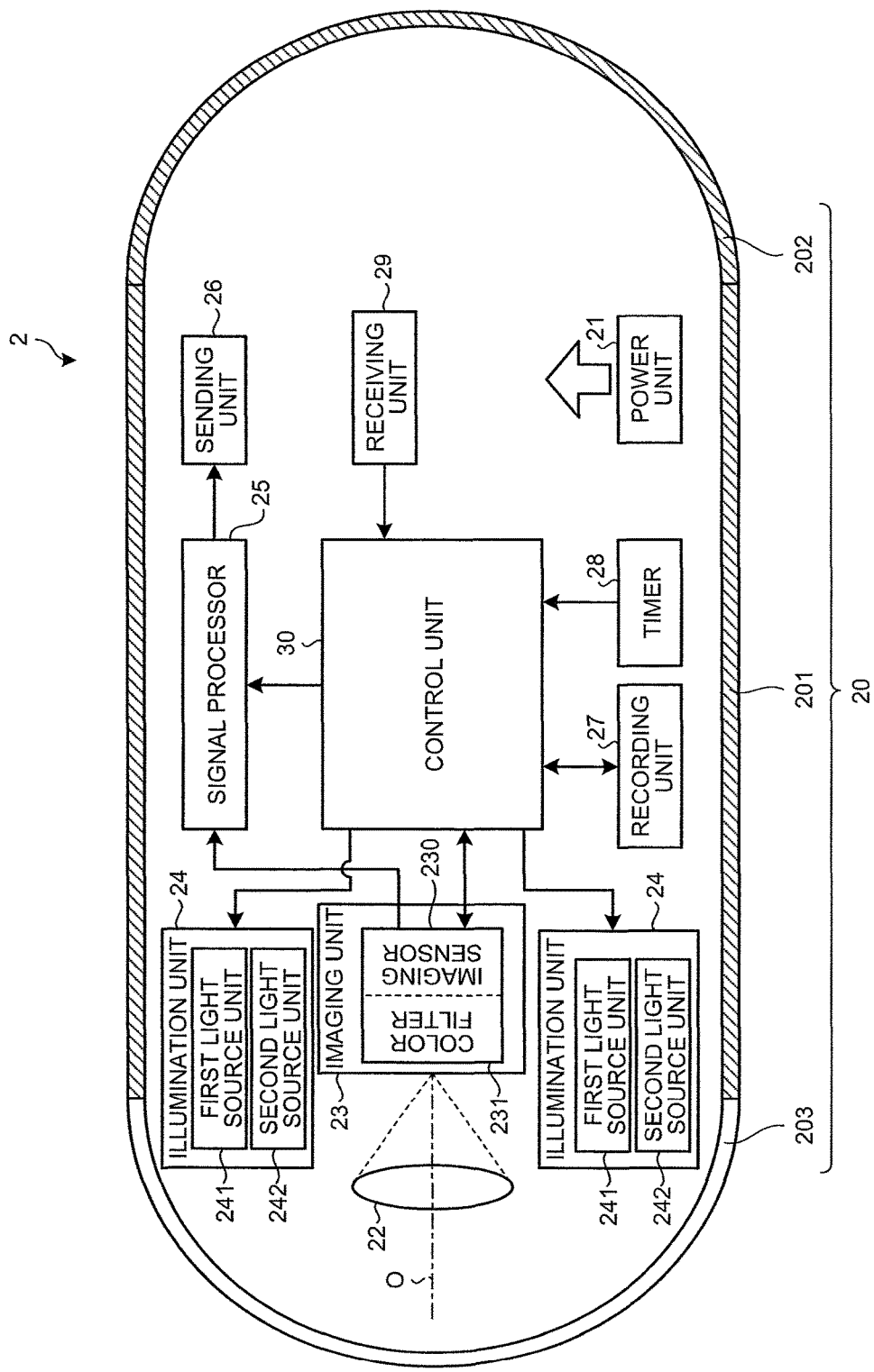
FIG. 2 is a block diagram illustrating a functional configuration of a capsule endoscope according to the first embodiment of the present disclosure.

Next, the detailed configuration of the capsule endoscope 2 described in FIG. 1 will be described. FIG. 2 is a block diagram illustrating a functional configuration of the capsule endoscope 2. The capsule endoscope 2 illustrated in FIG. 2 has a casing 20, a power unit 21, an optical system 22, an imaging unit 23, an illumination unit 24, a signal processor 25, a sending unit 26, a recording unit 27, a timer 28, a receiving unit 29, and a control unit 30.

The casing 20 has a capsule shape formed to have such a size as to allow itself to be easily introduced into the subject 100. The casing 20 has a cylindrical tube portion 201 and dome-shaped dome portions 202 and 203. The dome portions 202 and 203 cover both opening ends of the tube portion 201. Each of the tube portion 201 and the dome portion 202 is formed with the use of an opaque colored member that blocks visible light. The dome portion 203 is configured with the use of an optical member capable of transmitting light in a predetermined wavelength band such as visible light. The casing 20 formed of the tube portion 201 and the dome portions 202 and 203 contains the power unit 21, the optical system 22, the imaging unit 23, the illumination unit 24, the signal processor 25, the sending unit 26, the recording unit 27, the timer 28, the receiving unit 29, and the control unit 30 as illustrated in FIG. 2.

The power unit 21 supplies power to each component in the capsule endoscope 2. The power unit 21 is configured with the use of a primary battery or a secondary battery such as a button battery and a power circuit that boosts the electric power supplied from the button battery. The power unit 21 has a magnetic switch and switches an on/off state of the power by means of a magnetic field applied from the outside.

The optical system 22 is configured with the use of a plurality of lenses. The optical system 22 collects reflected light of illumination light radiated by the illumination unit 24 at an imaging surface of the imaging unit 23, and forms an object image. The optical system 22 is arranged in the casing 20 so that an optical axis coincides with a central axis O in a longitudinal direction of the casing 20.

Under the control of the control unit 30, the imaging unit 23 receives the object image formed at the light receiving surface by the optical system 22 and performs a photoelectric conversion, thereby generating the image data of the subject 100. More specifically, under the control of the control unit 30, the imaging unit 23 captures the subject 100 at a reference frame rate, for example, at a frame rate of 4 fps, and generates the image data of the subject 100. The imaging unit 23 is configured with the use of an imaging sensor 230 such as a charge coupled device (CCD) and a complementary metal oxide semiconductor (CMOS) and a color filter 231. The imaging sensor 230 performs the photoelectric conversion on light received by each of a plurality of pixels arranged in a two-dimensional pattern to generate an electric signal. In the color filter 231, a filter unit including a plurality of first band filters (hereinafter referred to as "broadband filters") and a second band filter (hereinafter referred to as a "narrowband filter") is arranged in association with the plurality of pixels. Each of the first band filters transmits light in a wavelength band of a primary color or a complementary color. The second band filter transmits narrowband light having a maximum value outside the range of the wavelength band of the light that passes through the first band filter.

Figure 3:
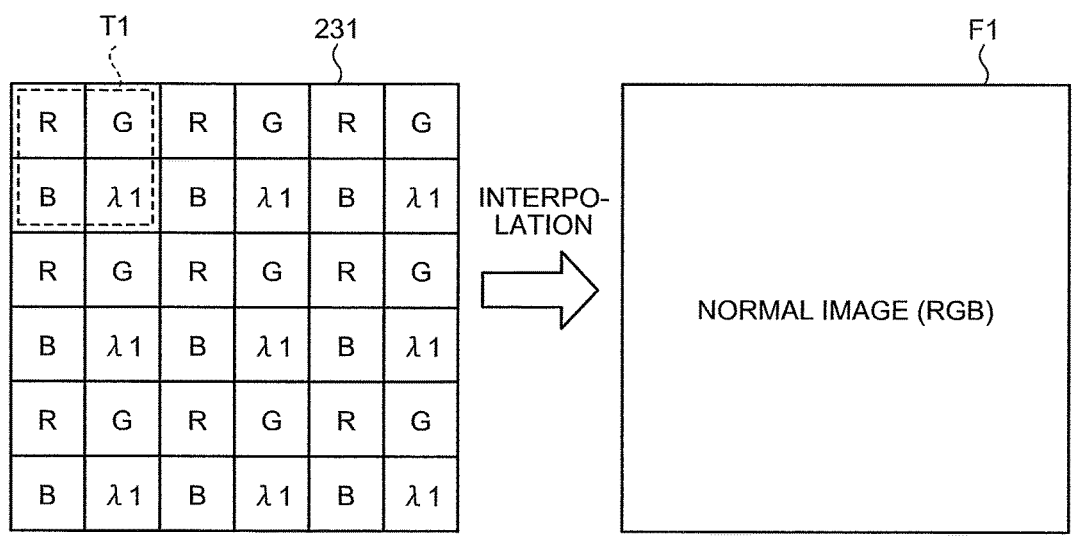
FIG. 3 is a diagram schematically illustrating a configuration of a color filter according to the first embodiment of the present disclosure.
Figure 3:
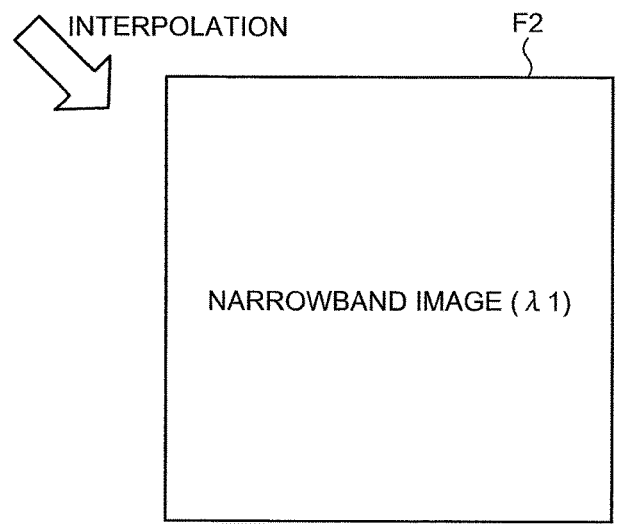

FIG. 3 is a diagram schematically illustrating a configuration of the color filter 231. As illustrated in FIG. 3, the color filter 231 is configured with the use of the filter unit including a set of arrayed filters T1, that is, a broadband filter R that transmits a red component, a broadband filter G that transmits a green component, a broadband filter B that transmits a blue component, and a narrowband filter $\lambda 1$ that transmits narrowband light having a maximum value of a transmission spectrum outside the range of the wavelength band of the light that passes through each of the broadband filters. As used herein, the wavelength band of the narrowband light in the first embodiment is 415 nm±30 nm. The image data generated by the imaging unit 23 using the color filter 231 configured as above are subjected to a predetermined image process (e.g., interpolation such as a demosaicing process) by the receiving device 4 or the image processing device 5, and thus converted into a colored normal image F1 and a narrowband special image F2. As used herein, the transmission spectrum is a wavelength spectrum in relation to transmittance of each filter. The transmittance of each filter of the color filter 231 will be described later in detail.

Under the control of the control unit 30, the illumination unit 24 radiates light to the object within an imaging field of the imaging unit 23 in synchronization with the frame rate of the imaging unit 23. The illumination unit 24 has a first light source unit 241 and a second light source unit 242.

The first light source unit 241 radiates light in the range of the transmission spectrum of each of the broadband filters R, G, and B. More specifically, the first light source unit 241 radiates white light. The first light source unit 241 is configured with the use of a white light emitting diode (LED) light source.

The second light source unit 242 radiates light having an upward projecting distribution of a wavelength spectrum in relation to the intensity and having a narrowband light spectrum (hereinafter referred to as a "narrow spectrum") narrower than the broadband. Specifically, the light is radiated such that an upper limit value and a lower limit value of a wavelength that are half a maximum value in the light spectrum are between an upper limit value and a lower limit value of a wavelength that are half a maximum value in the transmission spectrum of the narrowband filter $\lambda 1$. More specifically, the second light source unit 242 radiates such light that the upper limit value and the lower limit value of the wavelength that are half the maximum value in the narrow spectrum are between the upper limit value and the lower limit value that are half the maximum value in the transmission spectrum of the narrowband filter $\lambda 1$. Still more specifically, the second light source unit 242 radiates such light that the maximum value of the narrow spectrum is 415 nm±30 nm. The second light source unit 242 is configured with the use of an LED light source. The first light source unit 241 and the second light source unit 242 are configured by a single light source module.

The signal processor 25 performs a predetermined image process on the image data input from the imaging unit 23, and outputs the image data to the sending unit 26. As used herein, the predetermined image process is a noise reduction process and a gain-up process or the like.

The sending unit 26 wirelessly sends, to the outside, the pieces of image data sequentially input from the signal processor 25. The sending unit 26 is configured with the use of a sending antenna and a modulation circuit that performs a signal process such as a modulation on the image data and modulates the image data into a wireless signal.

The recording unit 27 records, for example, programs indicating various operations that are executed by the capsule endoscope 2 and identification information for identifying the capsule endoscope 2.

The timer 28 has a time measuring function. The timer 28 outputs time measuring data to the control unit 30.

The receiving unit 29 receives a wireless signal sent from the outside and outputs the wireless signal to the control unit 30. The receiving unit 29 is configured with the use of a receiving antenna and a demodulation circuit that performs a signal process such as a demodulation on the wireless signal and outputs the demodulated signal to the control unit 30.

The control unit 30 controls the operation of each component of the capsule endoscope 2. The control unit 30 causes the first light source unit 241 and the second light source unit 242 to radiate the beams of light simultaneously. The control unit 30 also causes the imaging sensor 230 to perform the capturing and generate the image data in synchronization with the radiation timing of the first light source unit 241 and the second light source unit 242. The control unit 30 is configured with the use of a central processing unit (CPU).

The capsule endoscope 2 configured as above successively captures the inside of the body cavity of the subject 100 at very small time intervals while moving through the body cavity of the subject 100. The capsule endoscope 2 then generates the pieces of image data of the inside of the subject 100 captured, and sequentially sends the pieces of image data to the receiving antenna unit 3.

Next, the relation between the transmittance of each filter that constitutes the above-mentioned color filter 231, intensity of the light radiated by the first light source unit 241, and intensity of the light radiated by the second light source unit 242 will be described.

Figure 4:
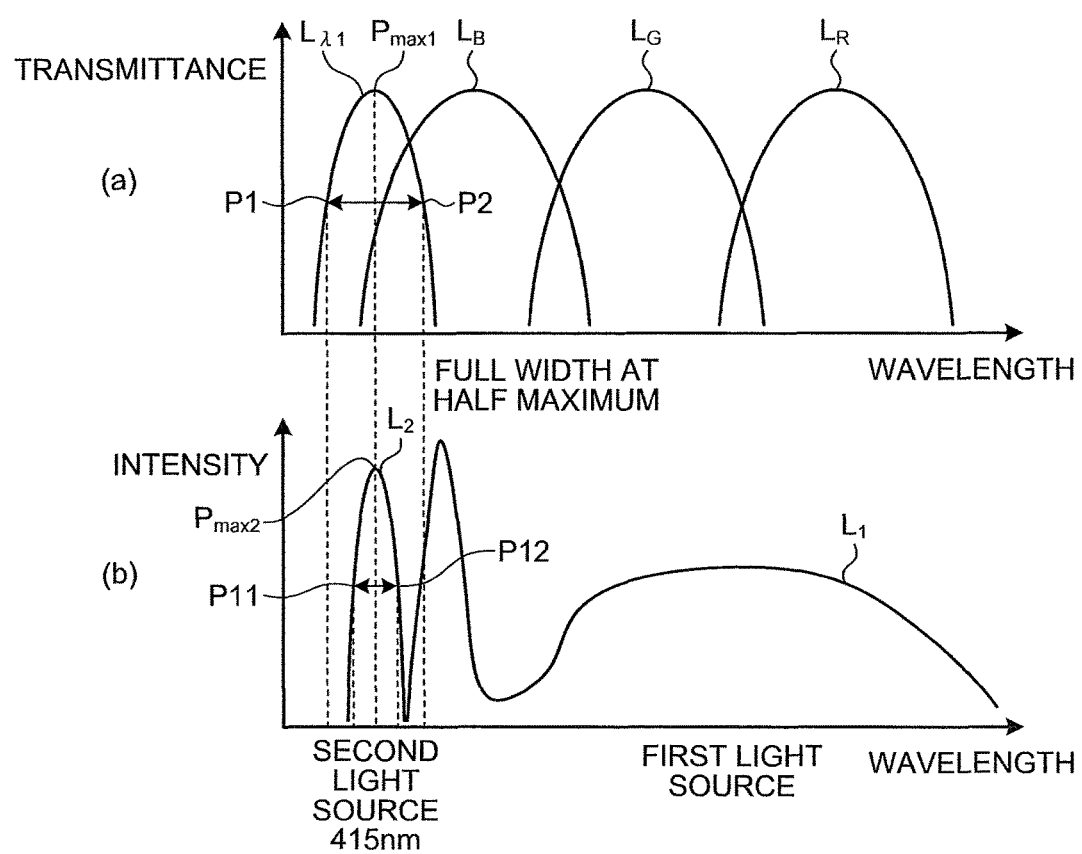
FIG. 4 is a diagram illustrating the relation between transmittance of each filter that constitutes the color filter and intensity of light radiated by an illumination unit according to the first embodiment of the present disclosure.

FIG. 4 is a diagram illustrating the relation between the transmittance of each filter that constitutes the color filter 231, the intensity of the light radiated by the first light source unit 241, and the intensity of the light radiated by the second light source unit 242. In FIG. 4, FIG. 4(a) illustrates the relation between the transmittance and the wavelength of each filter that constitutes the color filter 231, and FIG. 4(b) illustrates the relation between the wavelength and the intensity of the light spectrum radiated by the illumination unit 24. In FIG. 4(a), a curve $L_B$ illustrates the relation between the transmittance and the wavelength of the broadband filter B, a curve $L_G$ illustrates the relation between the transmittance and the wavelength of the broadband filter G, a curve $L_R$ illustrates the relation between the transmittance and the wavelength of the broadband filter R, and a curve $L_{\lambda 1}$ illustrates the relation between the transmittance and the wavelength of the narrowband filter λ1. Moreover, in FIG. 4(b), a curve $L_1$ illustrates the relation between the intensity and the wavelength of the light radiated by the first light source unit 241, and a curve $L_2$ illustrates the relation between the intensity and the wavelength of the light radiated by the second light source unit 242. The description of FIG. 4 is based on the assumption that the peak wavelength for the narrowband filter λ1 is 415 nm±30 nm.

As illustrated by the curve $L_1$ in FIG. 4, the first light source unit 241 radiates the light in the range of the transmission spectrum of each of the broadband filters B, G, and R. As illustrated by the curve $L_2$ in FIG. 4, the second light source unit 242 radiates such light that an upper limit value P12 and a lower limit value P11 of the wavelength that are half a maximum value $P_{max2}$ in the narrow spectrum are between a lower limit value P1 and an upper limit value P2 of the wavelength that are half a maximum value $P_{max1}$ in the transmission spectrum of the narrowband filter λ1. Furthermore, as illustrated by the curve $L_2$, the second light source unit 242 radiates such light that the maximum value $P_{max2}$ of the narrow spectrum substantially coincides with the maximum value $P_{max1}$ of the transmission spectrum of the narrowband filter λ1.

The beams of light radiated by the first light source unit 241 and the second light source unit 242 in this manner are reflected at the object and received by the imaging sensor 230 through the optical system 22 and the color filter 231. The electric signal (image information) subjected to the photoelectric conversion in the imaging sensor 230 undergoes the predetermined image process in the receiving device 4 or the image processing device 5, whereby the normal image F1 (refer to FIG. 3) and the narrowband special image F2 (refer to FIG. 3) may be obtained.

According to the above-described first embodiment, the second light source unit 242 radiates the light having the upward projecting distribution of the wavelength spectrum in relation to the intensity and having the narrow spectrum. Specifically, the light is radiated such that the upper limit value P12 and the lower limit value P11 of the wavelength that are half the maximum value $P_{max2}$ in the light spectrum are between the lower limit value P1 and the upper limit value P2 of the wavelength that are half the maximum value $P_{max1}$ in the transmission spectrum of the narrowband filter λ1. Therefore, the high-quality normal image may be obtained even when the normal image and the special image are simultaneously shot.

In addition, according to the first embodiment, images free from position misalignment may be obtained since the normal image and the narrowband special image may be simultaneously acquired.

Moreover, according to the first embodiment, an image process for aligning the images may be omitted when the normal image and the narrowband special image are superimposed since the normal image and the narrowband special image may be simultaneously acquired.

Furthermore, according to the first embodiment, the maximum value $P_{max2}$ of the narrow spectrum radiated by the second light source unit 242 substantially coincides with the maximum value $P_{max1}$ of the transmission spectrum of the narrowband filter λ1. Therefore, the narrowband image of higher quality may be acquired.

In addition, according to the first embodiment, the illumination unit 24 may be reduced in size since the first light source unit 241 and the second light source unit 242 are configured as a single light source module.

Second Embodiment

Next, a second embodiment of the present disclosure will be described. A difference between the second embodiment and the above-mentioned first embodiment is the transmission spectrum transmitted by the narrowband filter and the wavelength band of the light radiated by the second light source unit. Hereinafter, therefore, a configuration of a capsule endoscope according to the second embodiment will be described, and the relation between the transmittance of each filter that constitutes a color filter, the intensity of the light radiated by the first light source unit, and the intensity of the light radiated by the second light source unit according to the second embodiment will be described. Components that are identical to those of the capsule endoscope 2 according to the above-mentioned first embodiment are denoted by the same reference signs, and descriptions thereof are omitted.

Configuration of Capsule Endoscope

Figure 5:
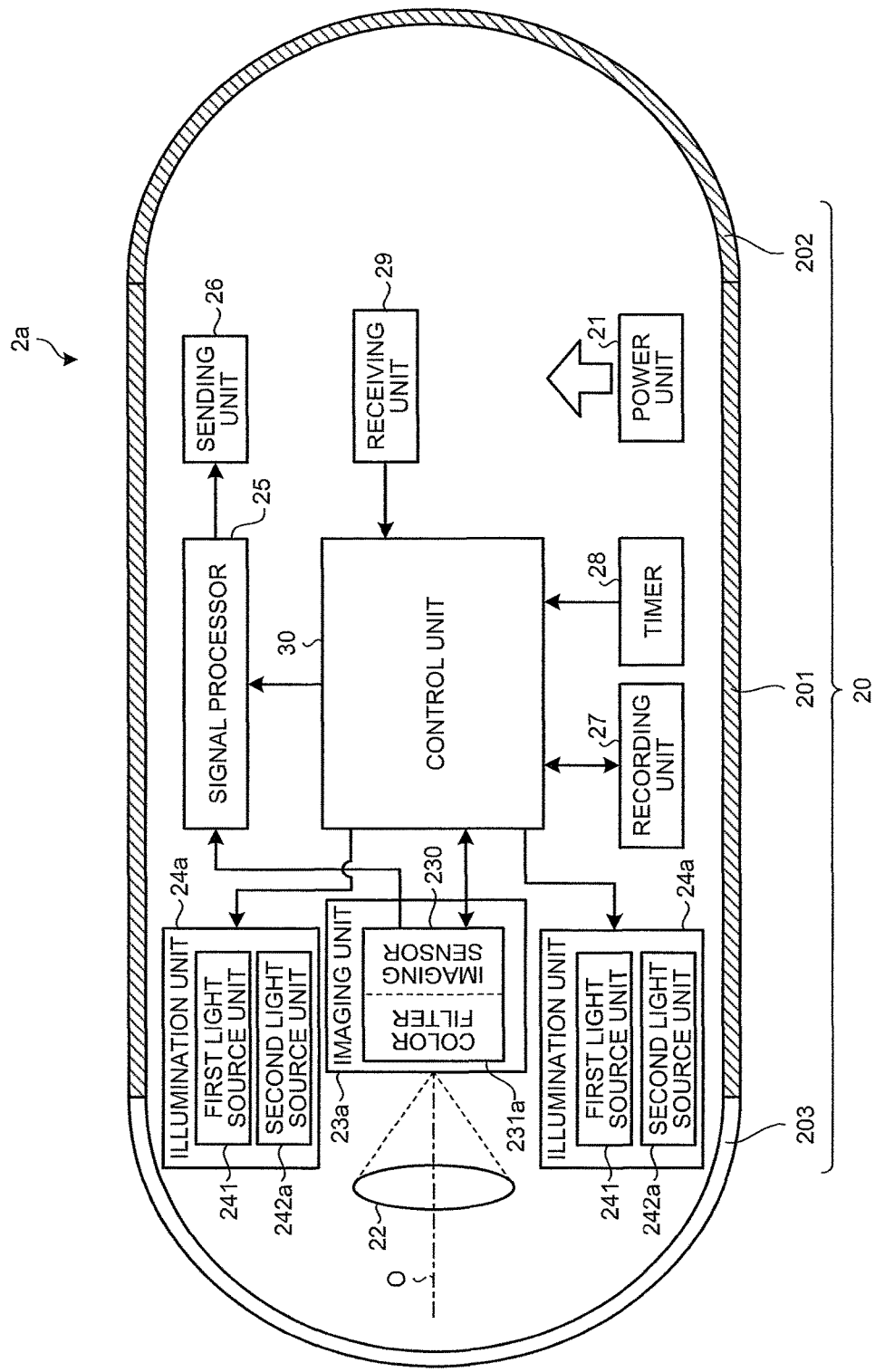
FIG. 5 is a block diagram illustrating a functional configuration of a capsule endoscope according to a second embodiment of the present disclosure.

FIG. 5 is a block diagram illustrating the functional configuration of the capsule endoscope according to the second embodiment. A capsule endoscope 2a illustrated in FIG. 5 includes an imaging unit 23a and an illumination unit 24a in place of the imaging unit 23 and the illumination unit 24 of the capsule endoscope 2 according to the above-mentioned first embodiment.

Under the control of the control unit 30, the imaging unit 23a receives the object image formed at the light receiving surface by the optical system 22 and performs the photoelectric conversion, thereby generating the image data of the subject 100. The imaging unit 23a has the imaging sensor 230 and a color filter 231a.

Figure 6:
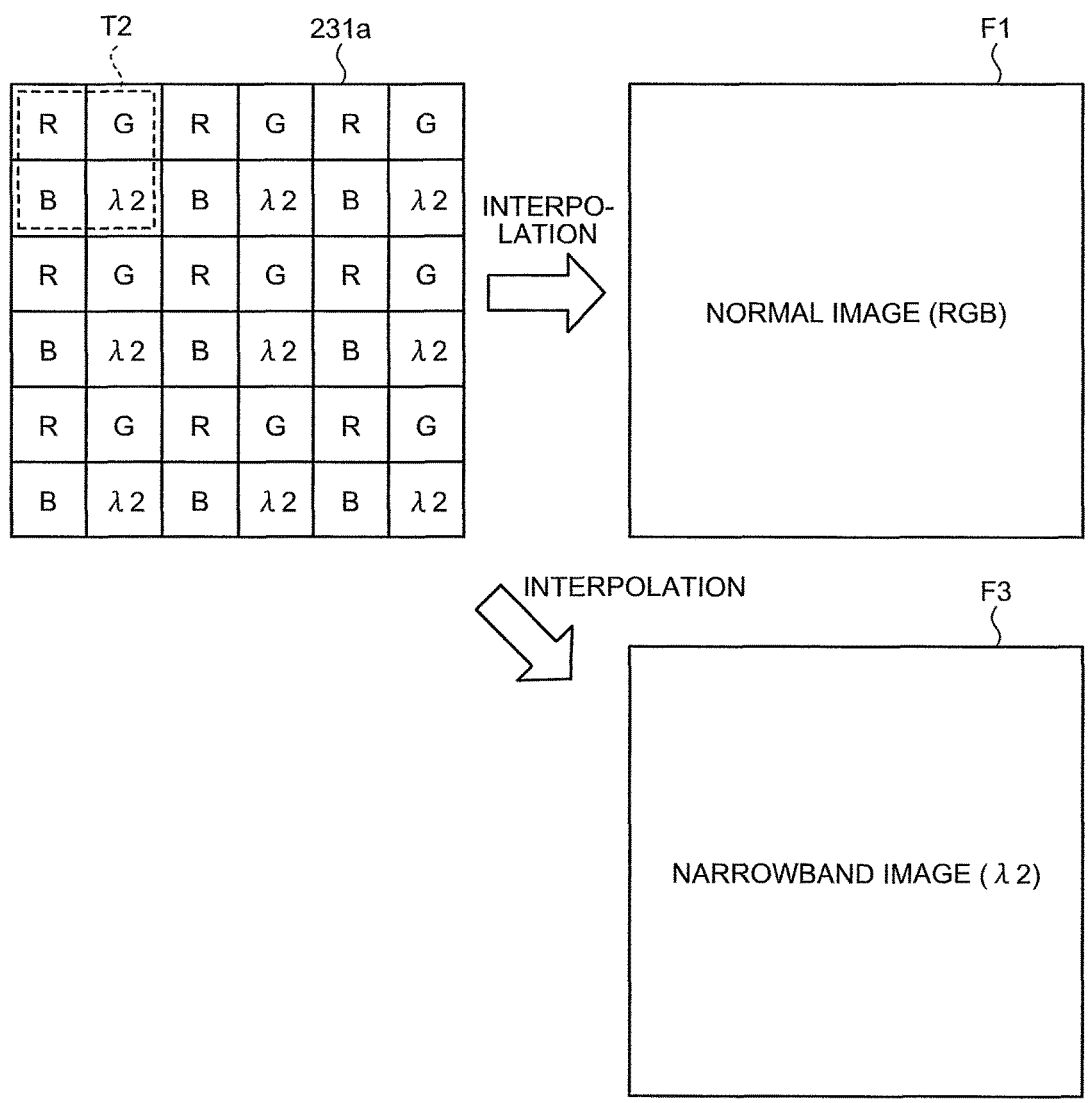
FIG. 6 is a diagram schematically illustrating a configuration of a color filter according to the second embodiment of the present disclosure.

FIG. 6 is a diagram schematically illustrating a configuration of the color filter 231a. As illustrated in FIG. 6, the color filter 231a is configured with the use of the filter unit including a set of arrayed filters T2, that is, the broadband filter R that transmits the red component, the broadband filter G that transmits the green component, the broadband filter B that transmits the blue component, and a narrowband filter λ2 that transmits narrowband light having a maximum value of a transmission spectrum outside the range of the wavelength band of the light that passes through each of the broadband filters. As used herein, the wavelength band of the narrowband light in the second embodiment is an infrared region, and more preferably a near-infrared region. The image data generated by the imaging unit 23a using the color filter 231a configured as above are subjected to the predetermined image process by the receiving device 4 or the image processing device 5, and thus converted into the colored normal image F1 and an infrared special image F3. The transmittance of each filter of the color filter 231a will be described later in detail.

Under the control of the control unit 30, the illumination unit 24a radiates light to the object within the imaging field of the imaging unit 23a in synchronization with the frame rate of the imaging unit 23a. The illumination unit 24a has the first light source unit 241 and a second light source unit 242a.

The second light source unit 242a radiates light having the upward projecting distribution of the wavelength spectrum in relation to the intensity and having the narrow spectrum. Specifically, the light is radiated such that an upper limit value and a lower limit value of a wavelength that are half a maximum value in the narrow spectrum are between an upper limit value and a lower limit value of a wavelength that are half a maximum value in the transmission spectrum of the narrowband filter λ2. More specifically, the second light source unit 242a radiates such light that the maximum value of the narrow spectrum is the infrared region. The second light source unit 242a is configured with the use of an LED light source. The first light source unit 241 and the second light source unit 242a are configured by a single light source module.

Next, the relation between the transmittance of each filter that constitutes the above-mentioned color filter 231a, the intensity of the light radiated by the first light source unit 241, and the intensity of the light radiated by the second light source unit 242a will be described.

Figure 7:
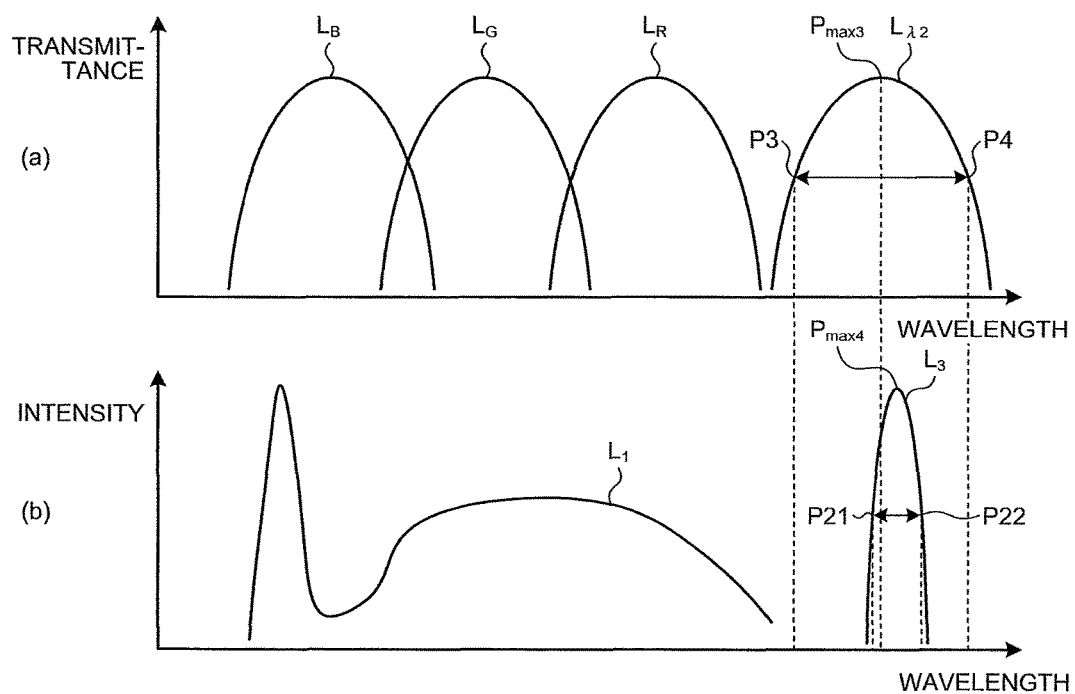
FIG. 7 is a diagram illustrating the relation between transmittance of each filter that constitutes the color filter and intensity of light radiated by an illumination unit according to the second embodiment of the present disclosure.

FIG. 7 is a diagram illustrating the relation between the transmittance of each filter that constitutes the color filter 231a, the intensity of the light radiated by the first light source unit 241, and the intensity of the light radiated by the second light source unit 242a. In FIG. 7, FIG. 7(a) illustrates the relation between the transmittance and the wavelength of each filter that constitutes the color filter 231a, and FIG. 7(b) illustrates the relation between the wavelength and the intensity of the light spectrum radiated by the illumination unit 24a. In FIG. 7(a), the curve $L_B$ illustrates the relation between the transmittance and the wavelength of the broadband filter B, the curve $L_G$ illustrates the relation between the transmittance and the wavelength of the broadband filter G, the curve $L_R$ illustrates the relation between the transmittance and the wavelength of the broadband filter R, and a curve $L_{\lambda 2}$ illustrates the relation between the transmittance and the wavelength of the narrowband filter λ2. Moreover, in FIG. 7(b), the curve $L_1$ illustrates the relation between the intensity and the wavelength of the light radiated by the first light source unit 241, and a curve $L_3$ illustrates the relation between the intensity and the wavelength of the light radiated by the second light source unit 242a. The description of FIG. 7 is based on the assumption that the peak wavelength for the narrowband filter λ2 is the infrared region.

As illustrated by the curve $L_1$ in FIG. 7, the first light source unit 241 radiates the light in the range of the transmission spectrum of each of the broadband filters B, G, and R. As illustrated by the curve $L_3$ in FIG. 7, the second light source unit 242a radiates the light having the upward projecting distribution of the wavelength spectrum in relation to the intensity. Specifically, the light is radiated such that an upper limit value P22 and a lower limit value P21 of the wavelength that are half a maximum value $P_{max4}$ in the narrow spectrum are between a lower limit value P3 and an upper limit value P4 of the wavelength that are half a maximum value $P_{max3}$ in the transmission spectrum of the narrowband filter λ2. Furthermore, as illustrated by the curve $L_3$ in FIG. 7, the second light source unit 242a radiates such light that the maximum value $P_{max4}$ of the narrow spectrum of the light is near the maximum value $P_{max3}$ of the transmission spectrum of the narrowband filter λ2.

According to the above-described second embodiment, the high-quality normal image may be obtained even when the normal image and the infrared special image are simultaneously shot, and an effect similar to that of the above-mentioned first embodiment may be obtained.

Third Embodiment

Next, a third embodiment of the present disclosure will be described. In the third embodiment, a plurality of narrowband filters of two types having different transmission spectra is provided in the color filter according to the above-mentioned first embodiment, and the illumination unit further has a third light source unit that radiates light having a narrow spectrum different from the wavelength band of the light radiated by the second light source unit. Hereinafter, therefore, a configuration of a capsule endoscope according to the third embodiment will be described, and the relation between the transmittance of each filter that constitutes a color filter, the intensity of the light radiated by the first light source unit, the intensity of the light radiated by the second light source unit, and the intensity of the light radiated by the third light source unit according to the third embodiment will be described. Components that are identical to those of the capsule endoscope 2 according to the above-mentioned first embodiment are denoted by the same reference signs, and descriptions thereof are omitted.

Configuration of Capsule Endoscope

Figure 8:
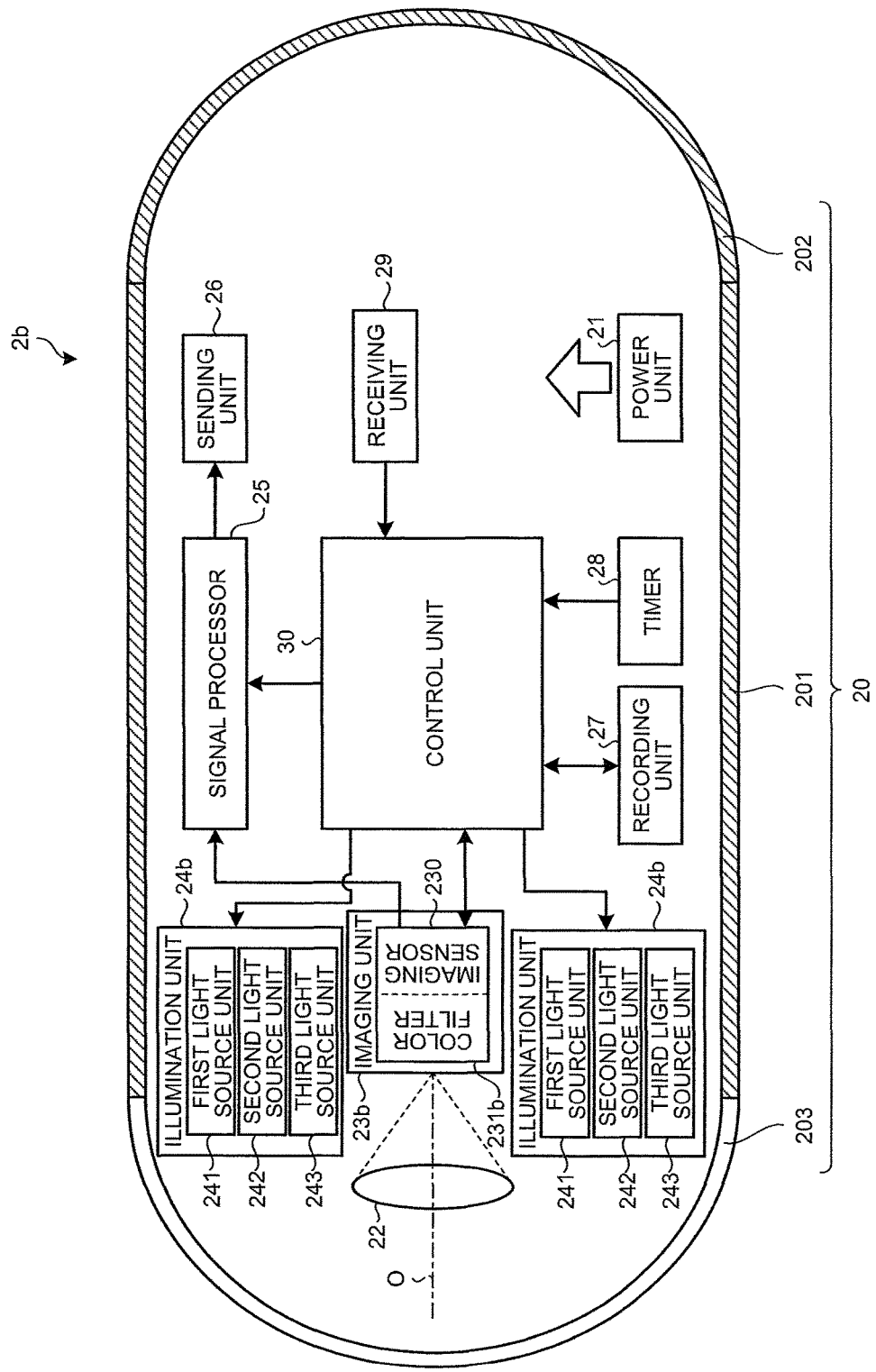
FIG. 8 is a block diagram illustrating a functional configuration of a capsule endoscope according to a third embodiment of the present disclosure.

FIG. 8 is a block diagram illustrating the functional configuration of the capsule endoscope according to the third embodiment. A capsule endoscope 2b illustrated in FIG. 8 includes an imaging unit 23b and an illumination unit 24b in place of the imaging unit 23 and the illumination unit 24 of the capsule endoscope 2 according to the above-mentioned first embodiment.

Under the control of the control unit 30, the imaging unit 23b receives the object image formed at the light receiving surface by the optical system 22 and performs the photoelectric conversion, thereby generating the image data of the subject 100. The imaging unit 23b has the imaging sensor 230 and a color filter 231b.

Figure 9:
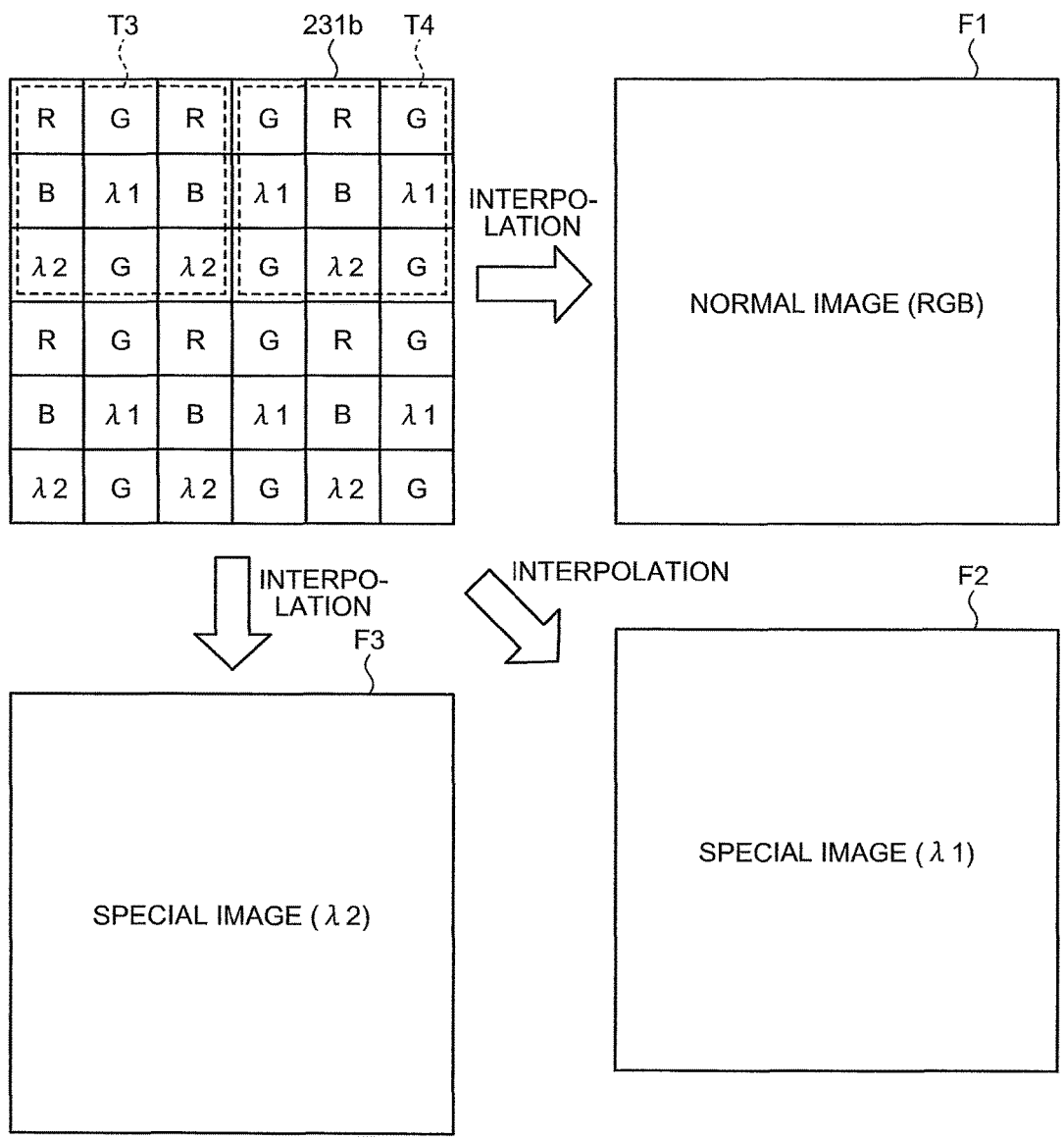
FIG. 9 is a diagram schematically illustrating a configuration of a color filter according to the third embodiment of the present disclosure.

FIG. 9 is a diagram schematically illustrating a configuration of the color filter 231b. As illustrated in FIG. 9, the color filter 231b is configured with the use of the filter unit including a set of filters T3 and the filter unit including a set of filters T4. Specifically, the set of filters T3 includes two broadband filters R that transmit the red component, two broadband filters G that transmit the green component, two broadband filters B that transmit the blue component, a single narrowband filter λ1 that transmits narrowband light having the maximum value of the transmission spectrum outside the range of the wavelength band of the light that passes through each of the broadband filters, and two narrowband filters λ2 (third band filters) that transmit narrowband light having the maximum value of the transmission spectrum outside the range of the wavelength band of the light that passes through each of the broadband filters R, G, and B and the narrowband filter λ1. The set of filters T4 includes a single broadband filter R, four broadband filters G, a single broadband filter B, two narrowband filters λ1, and a single narrowband filter λ2. The image data generated by the imaging unit 23b using the color filter 231b configured as above are subjected to the predetermined image process by the receiving device 4 or the image processing device 5, and thus converted into the colored normal image F1, the special image F2 (λ1), and the infrared special image F3 (λ2). The transmittance of each filter of the color filter 231b will be described later in detail.

Under the control of the control unit 30, the illumination unit 24b radiates light to the object within the imaging field of the imaging unit 23b in synchronization with the frame rate of the imaging unit 23b. The illumination unit 24b has the first light source unit 241, the second light source unit 242, and a third light source unit 243.

The third light source unit 243 radiates light having the upward projecting distribution of the wavelength spectrum in relation to the intensity and having the narrow spectrum. Specifically, the light is radiated such that the upper limit value and the lower limit value of the wavelength that are half the maximum value in the narrow spectrum are between the upper limit value and the lower limit value of the wavelength that are half the maximum value in the transmission spectrum of the narrowband filter λ2. More specifically, the third light source unit 243 radiates such light that the maximum value of the narrow spectrum is the infrared region. The third light source unit 243 is configured with the use of an LED light source. The first light source unit 241, the second light source unit 242, and the third light source unit 243 are configured by a single light source module.

Next, the relation between the transmittance of each filter that constitutes the color filter 231b, the intensity of the light radiated by the first light source unit 241, the intensity of the light radiated by the second light source unit 242, and the intensity of the light radiated by the third light source unit 243 will be described.

Figure 10:
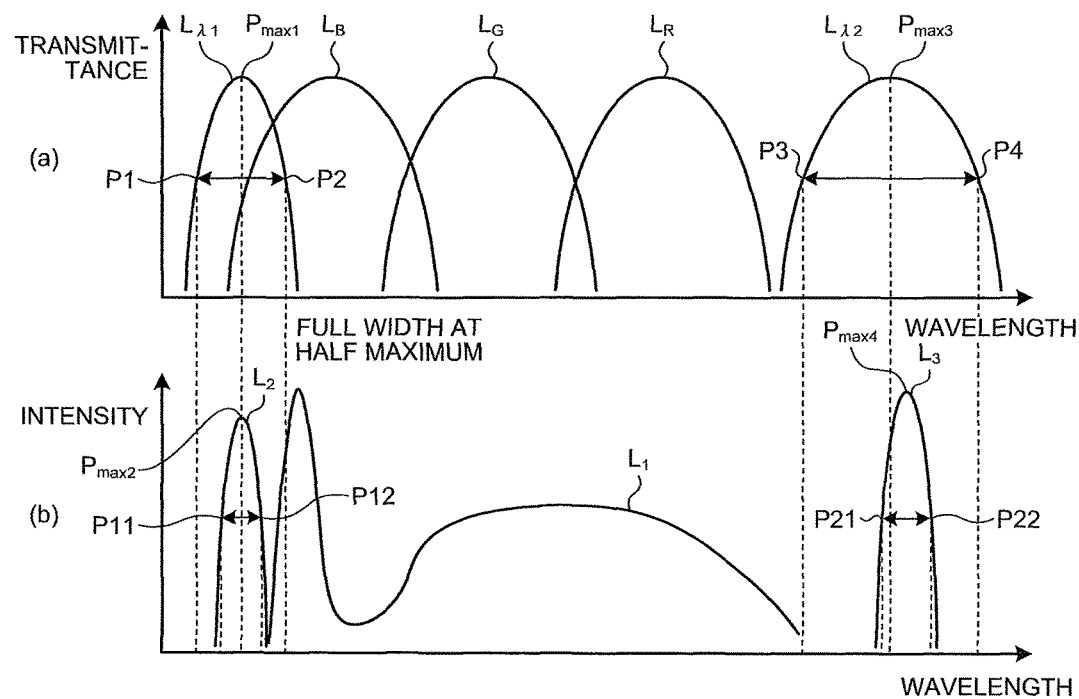
FIG. 10 is a diagram illustrating the relation between transmittance of each filter that constitutes the color filter and intensity of light radiated by an illumination unit according to the third embodiment of the present disclosure.

FIG. 10 is a diagram illustrating the relation between the transmittance of each filter that constitutes the color filter 231b, the intensity of the light radiated by the first light source unit 241, the intensity of the light radiated by the second light source unit 242, and the intensity of the light radiated by the third light source unit 243. In FIG. 10, FIG. 10(a) illustrates the relation between the transmittance and the wavelength of each filter that constitutes the color filter 231b, and FIG. 10(b) illustrates the relation between the wavelength and the intensity of the light spectrum radiated by the illumination unit 24b. In FIG. 10(a), the curve $L_B$ illustrates the relation between the transmittance and the wavelength of the broadband filter B, the curve $L_G$ illustrates the relation between the transmittance and the wavelength of the broadband filter G, the curve $L_R$ illustrates the relation between the transmittance and the wavelength of the broadband filter R, the curve $L_{\lambda 1}$ illustrates the relation between the transmittance and the wavelength of the narrowband filter λ1, and the curve $L_{\lambda 2}$ illustrates the relation between the transmittance and the wavelength of the narrowband filter λ2. Moreover, in FIG. 10(b), the curve $L_1$ illustrates the relation between the intensity and the wavelength of the light radiated by the first light source unit 241, the curve $L_2$ illustrates the relation between the intensity and the wavelength of the light radiated by the second light source unit 242, and the curve $L_3$ illustrates the relation between the intensity and the wavelength of the light radiated by the third light source unit 243. The description of FIG. 10 is based on the assumption that the peak wavelength for the narrowband filter λ1 is 415 nm±30 nm, and the peak wavelength for the narrowband filter λ2 is the infrared region.

As illustrated by the curve $L_1$ in FIG. 10, the first light source unit 241 radiates the light in the range of the transmission spectrum of each of the broadband filters B, G, and R. As illustrated by the curve $L_2$ in FIG. 10, the second light source unit 242 radiates the light having the upward projecting distribution of the wavelength spectrum in relation to the intensity. Specifically, the light is radiated such that the upper limit value P12 and the lower limit value P11 of the wavelength that are half the maximum value $P_{max2}$ in the narrow spectrum are between the lower limit value P1 and the upper limit value P2 of the wavelength that are half the maximum value $P_{max1}$ in the transmission spectrum of the narrowband filter λ1. Moreover, as illustrated by the curve $L_3$ in FIG. 10, the third light source unit 243 radiates the light having the upward projecting distribution of the wavelength spectrum in relation to the intensity. Specifically, the light is radiated such that the upper limit value P22 and the lower limit value P21 of the wavelength that are half the maximum value $P_{max4}$ in the narrow spectrum are between the lower limit value P3 and the upper limit value P4 of the wavelength that are half the maximum value $P_{max3}$ in the transmission spectrum of the narrowband filter λ2. Furthermore, as illustrated by the curve $L_3$ in FIG. 10, the third light source unit 243 radiates such light that the maximum value $P_{max4}$ of the narrow spectrum of the radiated light is near the maximum value $P_{max3}$ of the transmission spectrum of the narrowband filter λ2.

According to the above-described third embodiment, the high-quality normal image may be obtained even when the normal image, the narrowband special image, and the infrared special image are simultaneously shot, and an effect similar to that of the above-mentioned first embodiment may be obtained.

Fourth Embodiment

Next, a fourth embodiment of the present disclosure will be described. A difference between the fourth embodiment and the above-mentioned third embodiment is the transmission spectrum transmitted by the narrowband filter and the wavelength band of the light radiated by each of the second light source unit and the third light source unit. Hereinafter, therefore, a configuration of a capsule endoscope according to the fourth embodiment will be described, and the relation between the transmittance of each filter that constitutes a color filter, the intensity of the light radiated by the first light source unit, the intensity of the light radiated by the second light source unit, and the intensity of the light radiated by the third light source unit according to the fourth embodiment will be described. Components that are identical to those of the capsule endoscope 2 according to the above-mentioned first embodiment are denoted by the same reference signs, and descriptions thereof are omitted.

Configuration of Capsule Endoscope

Figure 11:
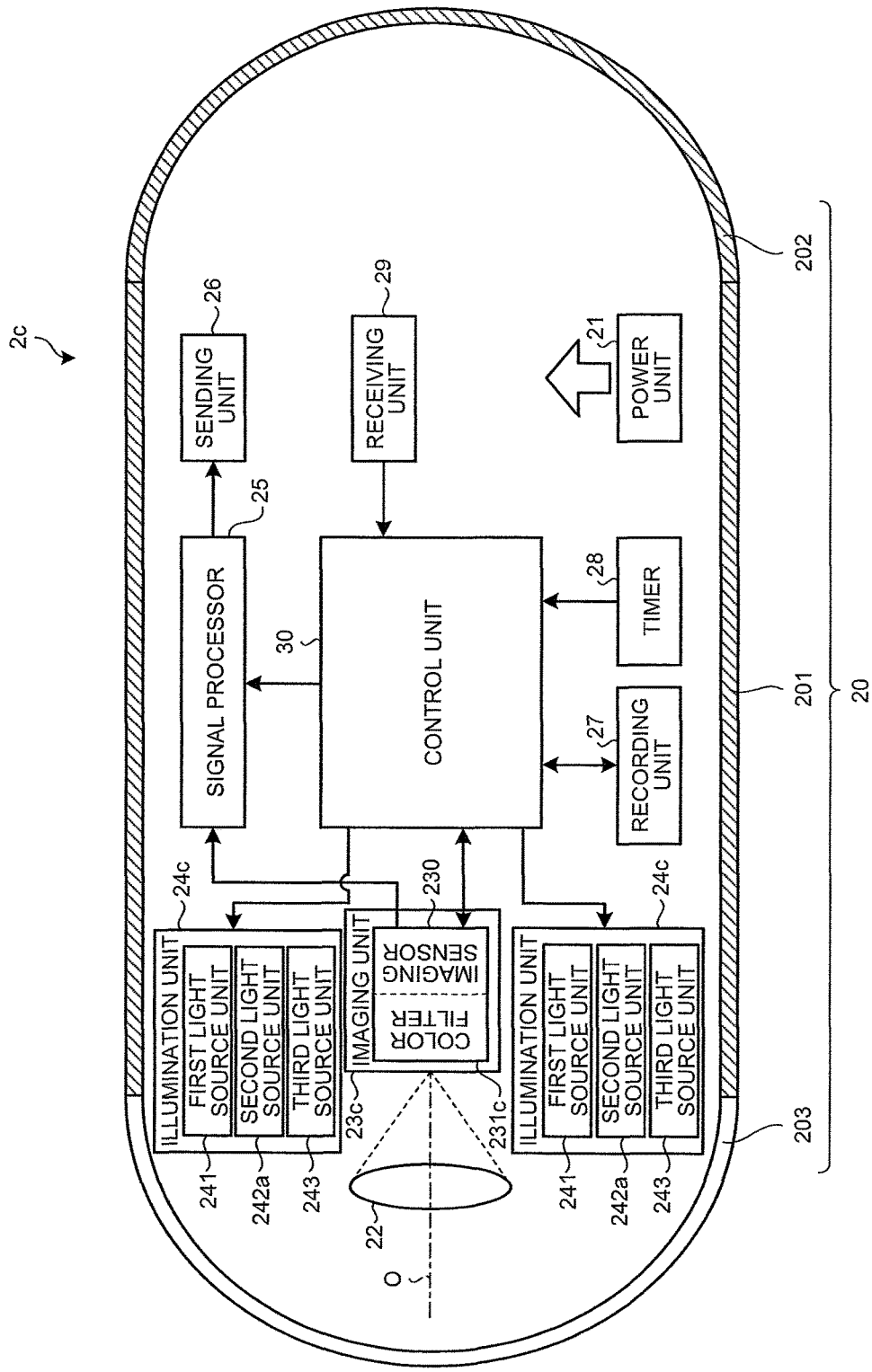
FIG. 11 is a block diagram illustrating a functional configuration of a capsule endoscope according to a fourth embodiment of the present disclosure.

FIG. 11 is a block diagram illustrating the functional configuration of the capsule endoscope according to the fourth embodiment. A capsule endoscope 2c illustrated in FIG. 11 includes an imaging unit 23c and an illumination unit 24c in place of the imaging unit 23b and the illumination unit 24b of the capsule endoscope 2b according to the above-mentioned third embodiment.

Under the control of the control unit 30, the imaging unit 23c receives the object image formed at the light receiving surface by the optical system 22 and performs the photoelectric conversion, thereby generating the image data of the subject 100. The imaging unit 23c has the imaging sensor 230 and a color filter 231c.

Figure 12:
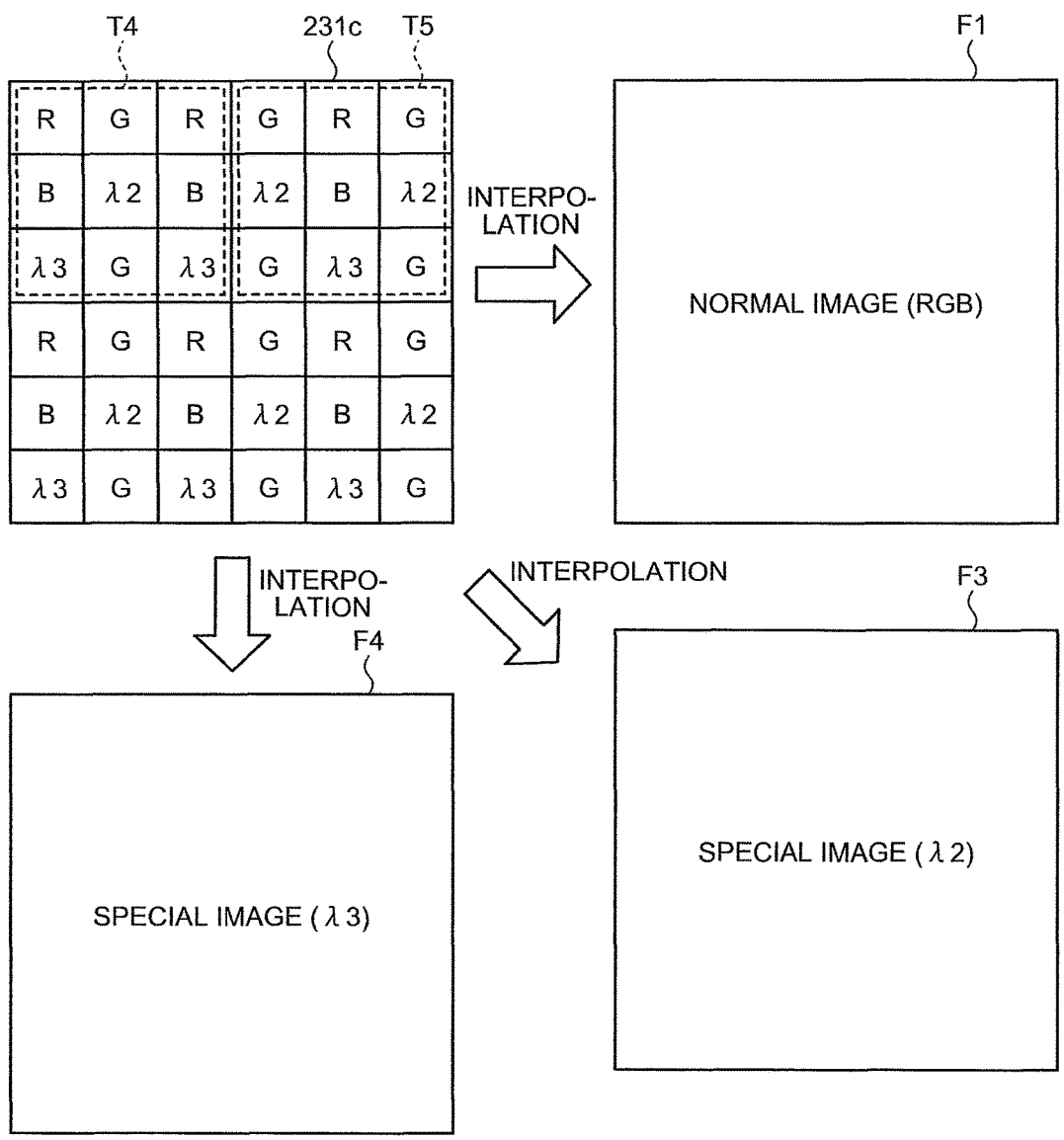
FIG. 12 is a diagram schematically illustrating a configuration of a color filter according to the fourth embodiment of the present disclosure.

FIG. 12 is a diagram schematically illustrating a configuration of the color filter 231c. As illustrated in FIG. 12, the color filter 231c is configured with the use of the filter unit including a set of filters T4 and the filter unit including a set of filters T5. Specifically, the set of filters T4 includes two broadband filters R that transmit the red component, two broadband filters G that transmit the green component, two broadband filters B that transmit the blue component, a single narrowband filter λ2 that transmits narrowband light having the maximum value of the transmission spectrum outside the range of the wavelength band of the light that passes through each of the broadband filters, and two narrowband filters λ3 (third band filters) that transmit narrowband light having a maximum value of a transmission spectrum outside the range of the wavelength band of the light that passes through each of the broadband filters R, G, and B and the narrowband filter λ2. The set of filters T5 includes a single broadband filter R, four broadband filters G, a single broadband filter B, two narrowband filters λ2, and a single narrowband filter λ3. The image data generated by the imaging unit 23c using the color filter 231c configured as above are subjected to the predetermined image process by the receiving device 4 or the image processing device 5, and thus converted into the colored normal image F1, the infrared special image F3 (λ2), and a near-infrared special image F4 (λ3). The transmittance of each filter of the color filter 231c will be described later in detail.

Under the control of the control unit 30, the illumination unit 24c radiates light to the object within the imaging field of the imaging unit 23c in synchronization with the frame rate of the imaging unit 23c. The illumination unit 24c has the first light source unit 241, the second light source unit 242a, and the third light source unit 243.

The third light source unit 243 radiates light having the upward projecting distribution of the wavelength spectrum in relation to the intensity and having the narrow spectrum. Specifically, the light is radiated such that an upper limit value and a lower limit value of a wavelength that are half a maximum value in the narrow spectrum are between an upper limit value and a lower limit value of a wavelength that are half a maximum value in the transmission spectrum of the narrowband filter λ3. More specifically, the third light source unit 243 radiates such light that the maximum value of the narrow spectrum is the near-infrared region. The third light source unit 243 is configured with the use of an LED light source. The first light source unit 241, the second light source unit 242a, and the third light source unit 243 are configured by a single light source module.

Next, the relation between the transmittance of each filter that constitutes the color filter 231c, the intensity of the light radiated by the first light source unit 241, the intensity of the light radiated by the second light source unit 242a, and the intensity of the light radiated by the third light source unit 243 will be described.

Figure 13:
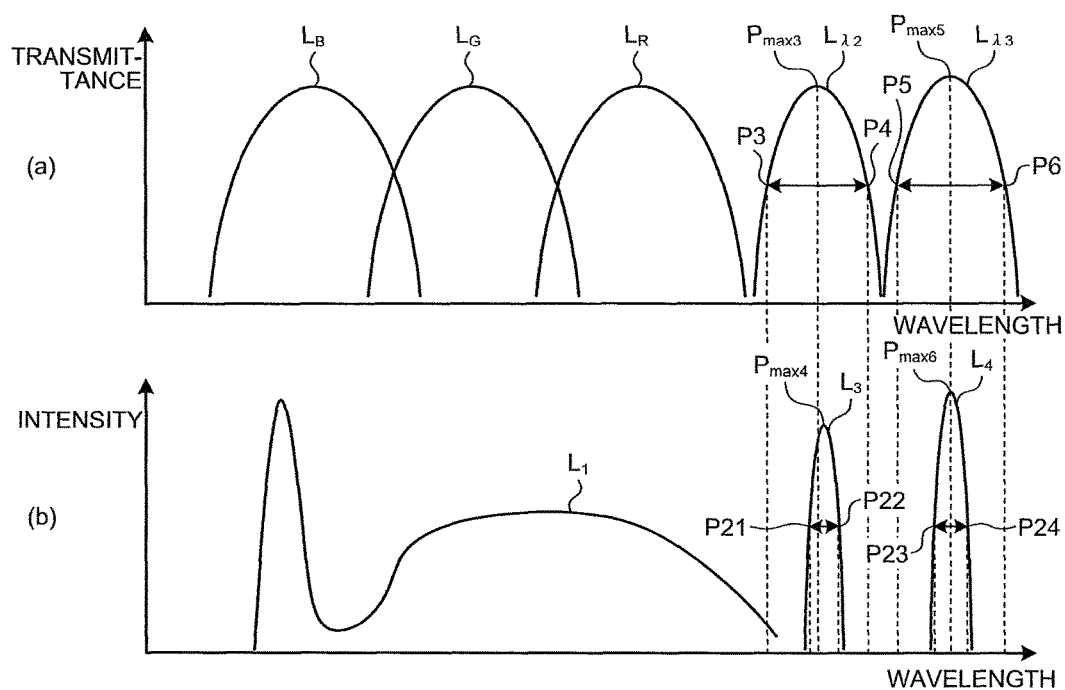
FIG. 13 is a diagram illustrating the relation between transmittance of each filter that constitutes the color filter and intensity of light radiated by an illumination unit according to the fourth embodiment of the present disclosure.

FIG. 13 is a diagram illustrating the relation between the transmittance of each filter that constitutes the color filter 231c, the intensity of the light radiated by the first light source unit 241, the intensity of the light radiated by the second light source unit 242a, and the intensity of the light radiated by the third light source unit 243. In FIG. 13, FIG. 13(a) illustrates the relation between the transmittance and the wavelength of each filter that constitutes the color filter 231c, and FIG. 13(b) illustrates the relation between the wavelength and the intensity of the light spectrum radiated by the illumination unit 24c. In FIG. 13(a), the curve $L_B$ illustrates the relation between the transmittance and the wavelength of the broadband filter B, the curve $L_G$ illustrates the relation between the transmittance and the wavelength of the broadband filter G, the curve $L_R$ illustrates the relation between the transmittance and the wavelength of the broadband filter R, the curve $L_{\lambda 2}$ illustrates the relation between the transmittance and the wavelength of the narrowband filter λ2, and a curve $L_{\lambda 3}$ illustrates the relation between the transmittance and the wavelength of the narrowband filter λ3. Moreover, in FIG. 13(b), the curve $L_1$ illustrates the relation between the intensity and the wavelength of the light radiated by the first light source unit 241, the curve $L_3$ illustrates the relation between the intensity and the wavelength of the light radiated by the second light source unit 242a, and a curve $L_4$ illustrates the relation between the intensity and the wavelength of the light radiated by the third light source unit 243. The description of FIG. 13 is based on the assumption that the peak wavelength for the narrowband filter λ2 is the infrared region, and the peak wavelength for the narrowband filter λ3 is the near-infrared region.

As illustrated by the curve $L_1$ in FIG. 13, the first light source unit 241 radiates the light in the range of the transmission spectrum of each of the broadband filters B, G, and R. As illustrated by the curve $L_3$ in FIG. 13, the second light source unit 242a radiates such light that the upper limit value P22 and the lower limit value P21 of the wavelength that are half the maximum value $P_{max4}$ in the narrow spectrum are between the lower limit value P3 and the upper limit value P4 of the wavelength that are half the maximum value $P_{max3}$ in the transmission spectrum of the narrowband filter λ2. Moreover, as illustrated by the curve $L_4$ in FIG. 13, the third light source unit 243 radiates such light that an upper limit value P24 and a lower limit value P23 of the wavelength that are half a maximum value $P_{max6}$ in the narrow spectrum are between a lower limit value P5 and an upper limit value P6 of the wavelength that are half a maximum value $P_{max5}$ in the transmission spectrum of the narrowband filter λ3. Furthermore, as illustrated by the curve $L_4$ in FIG. 13, the third light source unit 243 radiates such light that the maximum value $P_{max6}$ of the narrow spectrum of the radiated light is near the maximum value $P_{max5}$ of the transmission spectrum of the narrowband filter λ3.

According to the above-described fourth embodiment, the high-quality normal image may be obtained even when the normal image, the infrared special image, and the near-infrared special image are simultaneously shot, and an effect similar to that of the above-mentioned first embodiment may be obtained.

Another Embodiment

In the above-mentioned embodiments, the color filter includes the primary color filters. Alternatively, for example, complementary color filters (Cy, Mg, and Ye) that transmit beams of light having complementary wavelength components may be used. Moreover, a color filter (R, G, B, Or, and Cy) including the primary color filters and filters (Or and Cy) that transmit beams of light having wavelength components of orange and cyan may be used as the color filter. Furthermore, a color filter (R, G, B, and W) including the primary color filters and a filter (W) that transmits light having a wavelength component of white may be used.

In the above-mentioned embodiments, the narrowband filter that transmits a single kind of wavelength band is provided in the color filter. Alternatively, a plurality of narrowband filters may be provided in the color filter. For example, the narrowband filter λ1 of the above-mentioned first embodiment and the narrowband filter λ2 of the above-mentioned third embodiment may be provided.

In the above-mentioned embodiments, the capsule endoscope is described as an example of an imaging device. The present disclosure may also be applied to an endoscope having an insertion portion that is inserted into a subject.

The present disclosure may achieve an effect of obtaining a high-quality normal image even when the normal image and a special image are simultaneously shot.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging device comprising:
 an imaging sensor configured to perform a photoelectric conversion on light received by each of a plurality of pixels arranged in a two-dimensional pattern, to generate an electric signal;

a color filter in which a filter unit including a plurality of first band filters, a second band filter, and a third band filter is arranged in association with the plurality of pixels, each of the plurality of first band filters being configured to transmit light in a wavelength band of a primary color or a complementary color, the second band filter being configured to transmit narrowband light having a maximum value of a transmission spectrum outside a range of the wavelength band of the light that passes through each of the plurality of first band filters, and the third band filter being configured to transmit narrowband light having a maximum value of a transmission spectrum outside the range of the wavelength band of the light that passes through each of the plurality of first band filters and outside a wavelength band of the light that passes through the second band filter;

a first light source configured to radiate broadband light including a range of a transmission spectrum of each of the plurality of first band filters;

a second light source configured to radiate light having an upward projecting distribution of a wavelength spectrum in relation to intensity and having a narrowband light spectrum narrower than the broadband, the light being radiated such that an upper limit value and a lower limit value of a wavelength that are half a maximum value in the light spectrum are between an upper limit value and a lower limit value of a wavelength that are half the maximum value in the transmission spectrum of the second band filter;

a third light source configured to radiate light having an upward projecting distribution of a wavelength spectrum in relation to intensity and having a narrowband light spectrum narrower than the broadband, the light being radiated such that an upper limit value and a lower limit value of a wavelength that are half a maximum value in the light spectrum are between an upper limit value and a lower limit value of a wavelength that are half the maximum value in the transmission spectrum of the third band filter; and a processor configured to cause the first light source, the second light source, and the third light source to radiate beams of light simultaneously, wherein a peak wavelength of the light radiated by the second light source and a peak wavelength of the light radiated by the third light source are any two of an infrared region, a near-infrared region, and 415 nm±30 nm.

2. The imaging device according to claim 1, wherein the first light source, the second light source, and the third light source are configured by a single light source module.

3. A capsule endoscope system comprising:

a capsule endoscope including a capsule casing capable of being introduced into a subject and the imaging device according to claim 1 provided inside the casing; and a receiving device configured to wirelessly communicate with the capsule endoscope, receive a single image corresponding to the electric signal captured and output by the imaging sensor while the first light source, the second light source, and the third light source of the capsule endoscope radiate the beams of light simultaneously, and generate both a color image and a narrowband image from the single image.

4. An imaging device comprising:

imaging means for performing a photoelectric conversion on light received by each of a plurality of pixels arranged in a two-dimensional pattern, to generate an electric signal;

color filtering means for filtering light received by the plurality of pixels, the color filtering means including first filtering means, second filtering means, and third filtering means arranged in association with the plurality of pixels, the first filtering means being for transmitting light in a wavelength band of a primary color or a complementary color, the second filtering means being for transmitting narrowband light having a maximum value of a transmission spectrum outside a range of the wavelength band of the light that passes through the first filtering means, and the third filtering means being for transmitting narrowband light having a maximum value of a transmission spectrum outside the range of the wavelength band of the light that passes through the first filtering means and outside a wavelength band of the light that passes through the second filtering means;

first light emitting means for emitting broadband light including a range of a transmission spectrum of the first filtering means;

second light emitting means for emitting light having an upward projecting distribution of a wavelength spectrum in relation to intensity and having a narrowband light spectrum narrower than the broadband, the light being radiated such that an upper limit value and a lower limit value of a wavelength that are half a maximum value in the light spectrum are between an upper limit value and a lower limit value of a wavelength that are half the maximum value in the transmission spectrum of the second filtering means;

third light emitting means for emitting light having an upward projecting distribution of a wavelength spectrum in relation to intensity and having a narrowband light spectrum narrower than the broadband, the light being radiated such that an upper limit value and a lower limit value of a wavelength that are half a maximum value in the light spectrum are between an upper limit value and a lower limit value of a wavelength that are half the maximum value in the transmission spectrum of the third filtering means; and controlling means for controlling the first light emitting means, the second light emitting means, and the third light emitting means to radiate beams of light simultaneously, wherein a peak wavelength of the light emitted by the second light emitting means and a peak wavelength of the light radiated by the third light emitting means are any two of an infrared region, a near-infrared region, and 415 nm±30 nm.

5. The imaging device according to claim 4, wherein the first light emitting means, the second light emitting means, and the third light emitting means are configured by a single light source module.

6. A capsule endoscope system comprising:

a capsule endoscope including a capsule casing capable of being introduced into a subject and the imaging device according to claim 4 provided inside the casing; and receiving means for wirelessly communicating with the capsule endoscope, receiving a single image corresponding to the electric signal captured and output by the imaging means while the first light emitting means, the second light emitting means, and the third light emitting means of the capsule endoscope emit the beams of light simultaneously, and generating both a color image and a narrowband image from the single image.

* * * * *